United States Patent [19]
Kuck et al.

[11] Patent Number: 5,823,955
[45] Date of Patent: Oct. 20, 1998

[54] ATRIOVENTRICULAR VALVE TISSUE ABLATION CATHETER AND METHOD

[75] Inventors: Karl Heinz Kuck, Hamburg, Germany; Frank Nguyen, San Jose, Calif.

[73] Assignee: Medtronic CardioRhythm, San Jose, Calif.

[21] Appl. No.: 559,672

[22] Filed: Nov. 20, 1995

[51] Int. Cl.⁶ .................................. A61B 5/04; A61N 1/36
[52] U.S. Cl. ............................. 600/374; 606/41; 607/122
[58] Field of Search ........................... 128/642; 607/119, 607/122, 99; 606/46, 41; 604/95, 280–282; 600/374

[56] References Cited

U.S. PATENT DOCUMENTS

| | | |
|---|---|---|
| 4,522,212 | 6/1985 | Gelinas et al. . |
| 4,567,901 | 2/1986 | Harris . |
| 4,602,645 | 7/1986 | Barrington et al. . |
| 4,608,986 | 9/1986 | Beranek et al. . |
| 4,784,639 | 11/1988 | Patel . |
| 4,909,787 | 3/1990 | Danforth . |
| 5,058,595 | 10/1991 | Kern . |
| 5,190,050 | 3/1993 | Nitzsche . |
| 5,203,776 | 4/1993 | Durfee . |
| 5,215,540 | 6/1993 | Anderhub . |
| 5,238,005 | 8/1993 | Imran . |
| 5,263,493 | 11/1993 | Avitall . |
| 5,273,535 | 12/1993 | Edwards et al. . |
| 5,290,229 | 3/1994 | Paskar . |
| 5,299,574 | 4/1994 | Bower . |
| 5,306,262 | 4/1994 | Weldon . |
| 5,306,263 | 4/1994 | Voda . |
| 5,327,889 | 7/1994 | Imran . |
| 5,327,905 | 7/1994 | Avitall . |
| 5,354,297 | 10/1994 | Avitall . |
| 5,358,479 | 10/1994 | Wilson . |
| 5,368,564 | 11/1994 | Savage ................................. 607/122 X |
| 5,370,678 | 12/1994 | Edwards et al. . |
| 5,445,148 | 8/1995 | Jaraczewski et al. .................. 128/642 |
| 5,487,385 | 1/1996 | Avitall et al. ............................ 128/642 |
| 5,487,757 | 1/1996 | Truckai et al. .......................... 607/119 |
| 5,545,200 | 8/1996 | West et al. .............................. 607/122 |
| 5,549,581 | 8/1996 | Lurie et al. .......................... 607/122 X |
| 5,582,609 | 12/1996 | Swanson et al. .................... 607/101 X |

FOREIGN PATENT DOCUMENTS

WO 94/11057  5/1994  WIPO .

OTHER PUBLICATIONS

B. Olshansky, D.J. Wilber and R.J. Hardiman, "Artrial Flutter—Update on the Mechanism," PACE, vol., 15, pp. 2308–2309, Dec. 1992.

Kaster, "Artrial Flutter," Arrhythmias, pp. 110–114, 1994.

Boaz Avitall, et al., The Anatomical Determinants for the Design of Intracardiac Mapping and Ablation Catheters, PACE vol. 17, May 1994, Part 1, pp. 908–918.

Marketing Brochure ( in existence since Jun. 1995) introducing the "Angled Genesis Steerable Catheter," by Electro–Catheter Corporation of Rayway, New Jersey.

West, et al. "Steerable Electrode Catheter", Inthl Publ. WO 93/20877 published 28 Oct. 1993 (Copy 607/122).

*Primary Examiner*—Francis J. Jaworski
*Attorney, Agent, or Firm*—Townsend and Townsend and Crew LLP

[57] ABSTRACT

An atrioventricular valve tissue ablation catheter (2), especially suited for treating Mahaim fibers, includes a shaft (4) with a deflectable tip (20) at the distal end (6) and a handle (10) at the proximal end (8). The tip includes a distal segment (66) curving in one direction and a proximal segment (44) curving in the opposite direction so the distal segment causes the distal segment can engage tissue on either side of the annulus (92) of the tricuspid (or mitral) valve (90). Ablation energy can be supplied through the ablation electrodes (46, 70) simultaneously or one at a time to ablate tissue at the annulus without the need for moving the catheter. Mapping electrodes (38) are provided proximal of the ablation electrodes.

50 Claims, 7 Drawing Sheets

ATRIOVENTRICULAR VALVE TISSUE ABLATION CATHETER AND METHOD

CROSS REFERENCE TO RELATED APPLICATION

This application is related to U.S. patent application Ser. No. 08/429,429 filed May 1, 1995 for DUAL CURVE ABLATION CATHETER AND METHOD and now abandoned, the disclosure of which is incorporated by reference.

BACKGROUND OF THE INVENTION

It has long been known that the action of the heart depends upon electrical signals carried within the heart tissue. Sometimes these electrical signals become faulty. It has been found that ablating (burning) these cardiac conduction pathways in the region of the problem destroys the tissue to eliminate the faulty signal.

Electrophysiology (EP) catheters are catheters having one or more electrodes at their tips and are used for both diagnosis and therapy. The electrodes at the tips of EP catheters allow the physician to measure electrical signals along the surface of the heart (called mapping) and then, when necessary, ablate certain tissue using, typically, radio frequency (RF) energy directed to one or more high energy capable ablation electrodes.

SUMMARY OF THE INVENTION

The present invention is directed to an EP ablation catheter especially suited for ablating heart tissue on either side of the annulus of an atrioventricular (AV) valve. This technique could be useful to terminate a tachycardia caused by an accessory pathway from atrial to ventricular tissue. Some of these accessory pathways fall into the group "Mahaim fibers," commonly found on the right side of the heart at the right atrioventricular valve, also known as the tricuspid valve. However, the catheter could also be useful at the left side of the heart at the left atrioventricular valve, also called the mitral valve. The electrodes are potentially useful for mapping Mahaim fibers along the ventricular wall, or for mapping other regions of the heart. The catheter is designed to remain in place and provide firm electrode contact during mapping and ablation despite respiratory, cardiac or blood motion during the ablation.

The ablation catheter includes a shaft having proximal and distal ends with a deflectable tip at the distal end and a handle at the proximal end. Pulling on a manipulator wire, passing through a lumen in the shaft and attached to the distal end of the shaft, causes the proximal segment of the tip to curve. The distal segment can be preformed to create the desired hook or lip-shaped curvature; the distal end can also be curved using a manipulator wire as well. The proximal and distal segments curve in opposite directions so that when properly positioned, the proximal curve segment is passed through the AV valve to help stabilize the catheter and to place mapping electrodes against ventricular tissue. The distal segment engages the tissue at the annulus of the AV valve to be ablated. Ablation energy is preferably supplied through two ablation electrodes, preferably one at a time, to ablate the tissue on either side of the annulus of the AV valve without the need for moving the catheter back and forth across the valve, once in position.

A rotatable core wire, passing the central lumen and secured to the tip of the shaft, may be used to permit a torquing force to be applied to the distal end of the shaft without rotating the entire catheter. The temperature of the ablation electrodes is preferably monitored, such as using thermocouple wires, to permit enhanced control over the ablation temperatures.

One of the advantages of the invention is achieved when a series of ablation electrodes instead of one long electrode is used to ablate the cardiac tissue. Making the ablation electrodes electrically isolated from one another and allowing them to be individually powered permits a lower power ablation energy source to be used than would be required if the multiple ablation electrodes were replaced by one long electrode or if the multiple ablation electrodes were all powered simultaneously. Also, the use of multiple electrodes allows bipolar recording to be conducted. Of course, if a power source has sufficient capacity to simultaneously power more than one ablation electrode, this can be done also.

Other features and advantages of the invention will appear from the following description in which the preferred embodiment has been discussed in detail in conjunction with the accompanying drawings.

DESCRIPTION OF THE PREFERRED EMBODIMENT

Figures 1, 1A, 1B, 1C:
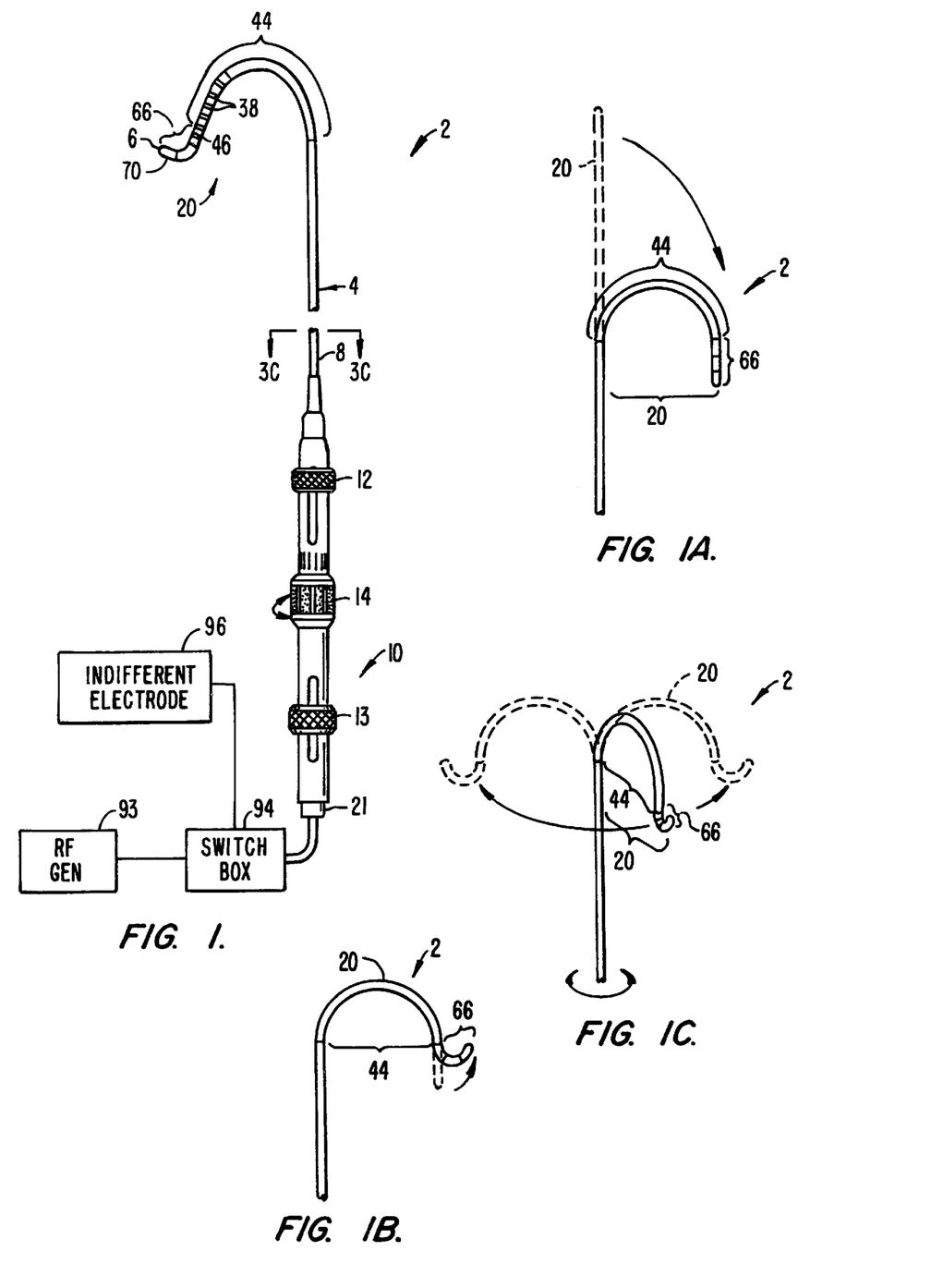
FIG. 1 is an overall view of an atrioventricular valve tissue ablation catheter made according to the invention.
FIG. 1A is a simplified view of the tip of the catheter showing the movement of the proximal segment from the straight, dashed line position to the curved, solid line position.
FIG. 1B is similar to FIG. 1A but shows the movement of the distal segment from the straight, dashed line position to the curved, solid line position.
FIG. 1C shows the lateral deflection of the catheter tip of FIG. 1B from the solid line position to the dashed line positions.
Figure 3A:
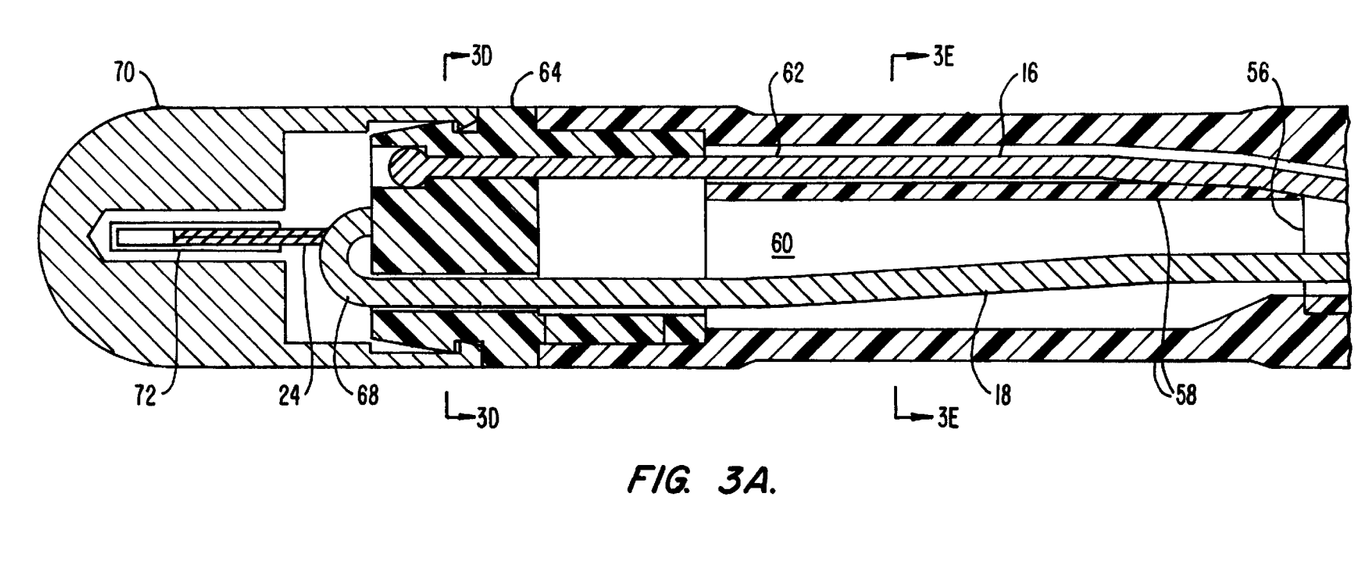
FIGS. 3A and 3B are enlarged longitudinal cross-sectional views of a portion of the tip of the catheter of FIG. 1 omitting the electrical conductor and thermocouple wires passing through the central lumen of the body of the catheter shaft and showing one ablation-capable tip electrode in FIG. 3A and one ablation-capable band electrode and two mapping electrodes in FIG. 3B.

FIG. 1 illustrates an anatomically-conforming, dual curve ablation catheter, in particular an atrioventricular (AV) valve tissue ablation catheter 2, including a catheter shaft 4 having a distal end 6 and a proximal end 8. Shaft 4 has an outside diameter of about 0.052 inch (1.32 mm) to 0.1040 inch (2.64 mm) and a length of about 50 mm to 110 mm. Proximal end 8 is mounted to a handle 10 having axially slidable manipulator rings 12, 13 and a rotatable lateral deflection ring 14 operably connected to proximal and distal manipulator wires 17, 16 and a core wire 18, respectively, the wires shown in FIGS. 3A and 3B. Sliding manipulator rings 12, 13 cause a deflectable tip 20 of catheter shaft 4 to deflect as shown in FIGS. 1A and 1B between, for example, the solid-line and dashed-line positions of FIG. 1B. Rotating ring 14 causes lateral deflection of tip 20 through the torquing action of core wire 18, as shown in FIG. 1C.

Figure 3B:
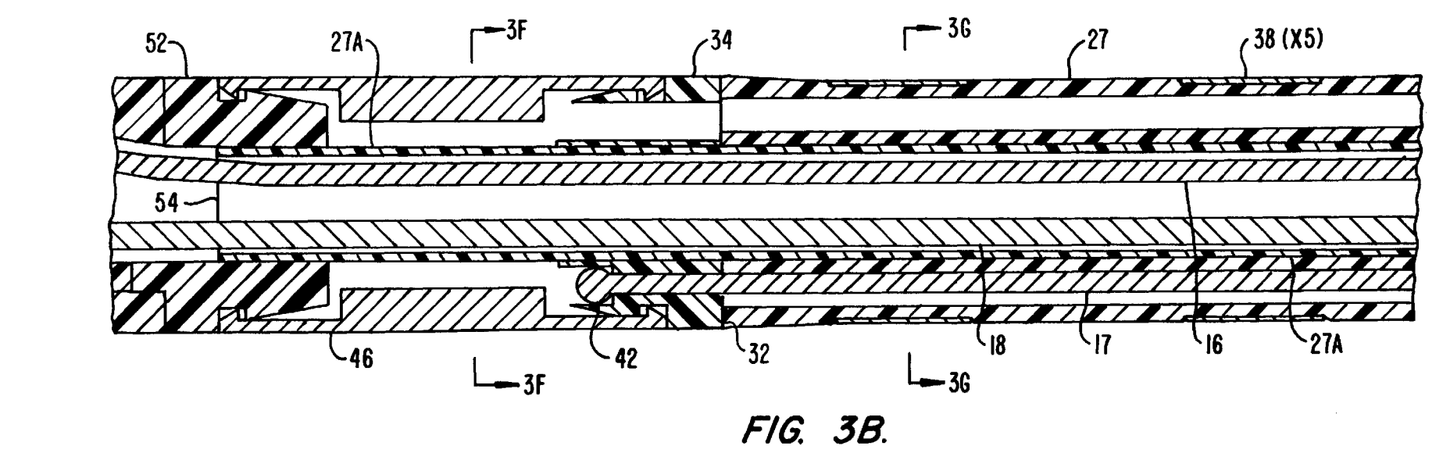
Figure 3C:
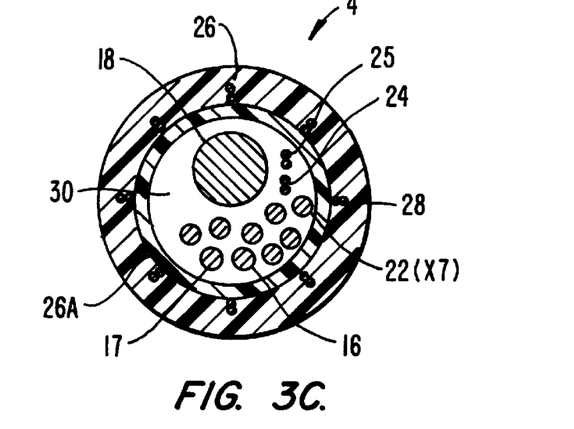
FIG. 3C is an enlarged transverse cross-sectional view of a segment of the catheter shaft taken along line 3C—3C of FIG. 1.

Handle 10 also includes an electrical connector 21 connected to seven electrical conductors 22 and two pairs of thermocouple wires 24, 25, conductors 22 and wires 24, 25 being shown in FIG. 3C. Handle 10 may be of a conventional design, or as shown in U.S. Pat. No. 5,318,525 or in U.S. Pat. No. 5,545,200, the disclosures of which are incorporated by reference.

The portion of shaft 4 proximal of deflectable tip 20, see FIG. 3C, is capable of good torque transmission to permit controlled placement of tip 20 at the target site as discussed below. Such proximal portion of the shaft 4 includes an outer jacket 26, preferably made of higher durometer Pebax®, such as 55-75D, reinforced by braided stainless steel wires 28. Pebax® is a polyamide polyether block copolymer made by Elf Atochem, Inc. of Philadelphia, Pa. A polyimide or ULTEMM tubular layer 26A, such as that sold by Hudson or General Electric, is positioned within the proximal central lumen 30 of shaft 4 and houses core wire 18, electrical conductors 22, thermocouple wires 24, 25 and manipulator wires 16, 17.

If desired, one or more axially slidable core wires could be used, the distal ends of the core wires being positionable at different axial positions along tip 20; doing so would permit the size of the curves of tip 20 to be changed. An example of a catheter with a variable curve tip is described in U.S. Pat. No. 5,565,200 for Steerable Electrophysiology Catheter, the disclosure of which is incorporated by reference.

The distal end 32 of shaft 4, see FIG. 3B, lies adjacent an insulator 34 made of PEEK (poly-ether-ether-keytone) or other hard, temperature-resistant material. Insulator 34 is bonded to distal end 32 of shaft 4 by heat fusing or adhesive.

Figure 3D:
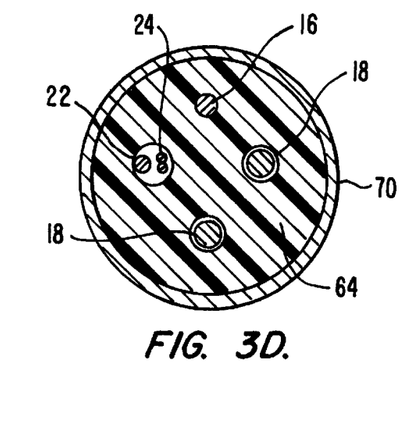
FIGS. 3D and 3E are transverse cross-sectional views taken along lines 3D—3D and 3E—3E in FIG. 3A.
Figure 3E:
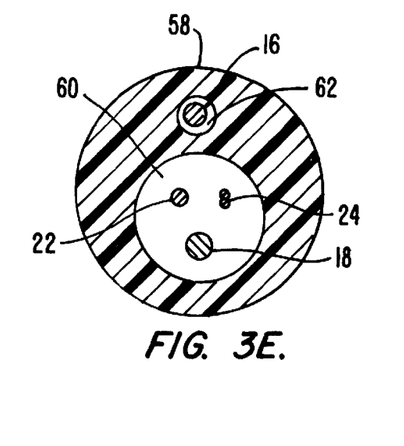
Figure 3F:
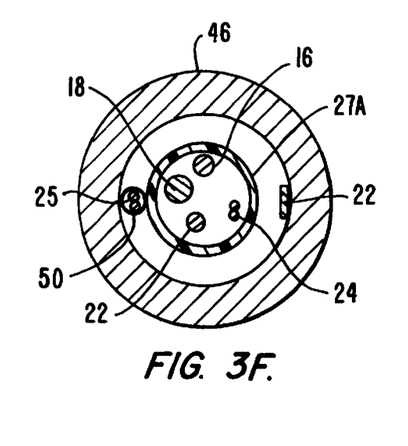
FIGS. 3F and 3G are transverse cross-sectional views taken along lines 3F—3F and 3G—3G in FIG. 3B.
Figure 3G:
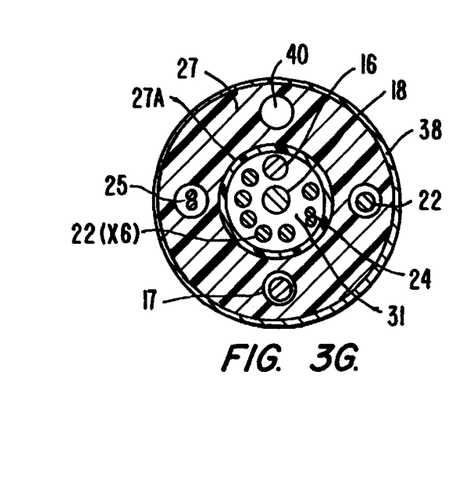

FIG. 3G illustrates a cross-sectional view of catheter shaft 4 adjacent distal end 32 passing through a band mapping electrode 38, five mapping electrodes 38 being positioned along catheter shaft 4 adjacent distal end 32. Each electrode 38 is connected to an electrical conductor 22, typically by soldering or welding techniques. In FIG. 3C all the wires and conductors are housed within proximal central lumen 30. In FIG. 3G some of these elements are housed within one of four satellite lumens 40 formed in outer jacket 26. For example, proximal manipulator wire 17, one pair of thermocouple wires 25 and one of the electrical conductors 22 pass within one of satellite lumens 40 at the position of FIG. 3G; the remainder of the wires and conductors pass within distal central lumen 31.

Proximal insulator 34 has five bores or lumens which generally align with the corresponding lumens 30, 40 formed in outer jacket 26 of shaft 4. Proximal insulation 34 is preferably mounted to outer tubing 27 and inner tubing 27A by means of thermal bond or adhesive. Proximal insulator 34 is preferably mounted to electrode 46 by means of mechanical interlock and/or adhesive. Manipulator wire 17 passes through one of the lumens in insulator 34 as shown in FIG. 3B and is secured therein by a large ball end 42 formed at the distal end of wire 17 so that pulling on manipulator wire 17 using manipulator ring 12 creates the curve in the proximal segment 44 of tip 20. See FIG. 1A. FIG. 3F illustrates the passing core wire 18, manipulator wire 16, one pair of thermocouple wires 24 and one electrical connector 22 within tubing 27A separated from cylindrical ablation-capable electrode 46. One of the electrical conductors 22 is soldered or welded to electrode 46 while one of the pairs of thermocouple wires 24 is positioned adjacent electrode 46 using a thermally conductive but electrical insulating tube 50, such as polyimide, to permit the temperature of electrode 46 to be monitored.

An insulator 52, also preferably made of PEEK, is mounted to the distal end of electrode 46 preferably using a mechanical interlock and/or adhesive. The distal end 54 of tube 27A is housed within and bonded to insulator 52 through the use of appropriated adhesive, thermal bond, or other appropriate methods. The distal end 56, see FIG. 3A, of insulator 52 is secured to a tubing segment 58 made of 35D Pebax®. Segment 58 has two major lumens, a central lumen 60, through which core wire 18, the second pair of thermocouple wires 24 and electrical conductor 22 pass, and an offset lumen 62, through which distal manipulator wire 16 passes. Note that only core wire 18 is shown passing within central lumen 60 in FIG. 3A. Segment 58 terminates at and is bonded thermally or adhesively to an insulator 64, also made PEEK, which serves as a terminus for distal manipulator wire 16 and core wire 18. Manipulation of manipulator ring 13 causes manipulator 16 to be pulled, thus causing the distal segment 66 of tip 22 to be pulled into the reverse curve shown in FIGS. 1 and 1B. The distal end 68 of core wire 18 is doubled back over and inserted back into an opening, not shown, in insulator 64. Manipulation of rotatable lateral deflection ring 14 causes the lateral movement of tip 20 as suggested in FIG. 1B. The final electrical conductor 22 (not shown in FIG. 3A) is electrically connected to tip electrode 70, typically by soldering or welding. The second thermocouple wire pair 24 is housed in a polyimide insulator tubing 72 within a recess 74 formed into electrode 70 and is secured in the recess using a suitable thermally conducting, electrically insulating adhesive, not shown.

Electrodes 38, 46, 70 are preferably made of platinum while manipulator wires 16, 17 and core wire 18 are preferably stainless steel. Manipulator wires 16, 17 are preferably coated with PTFE to reduce sliding friction.

The length of proximal segment 44 of tip 20 is preferably about 3 to 10 times, and more preferably about 5 times, the length of distal segment 66. In one preferred embodiment proximal and distal segments 44, 66 are about 70 mm and 15 mm long, respectively.

Figure 4:
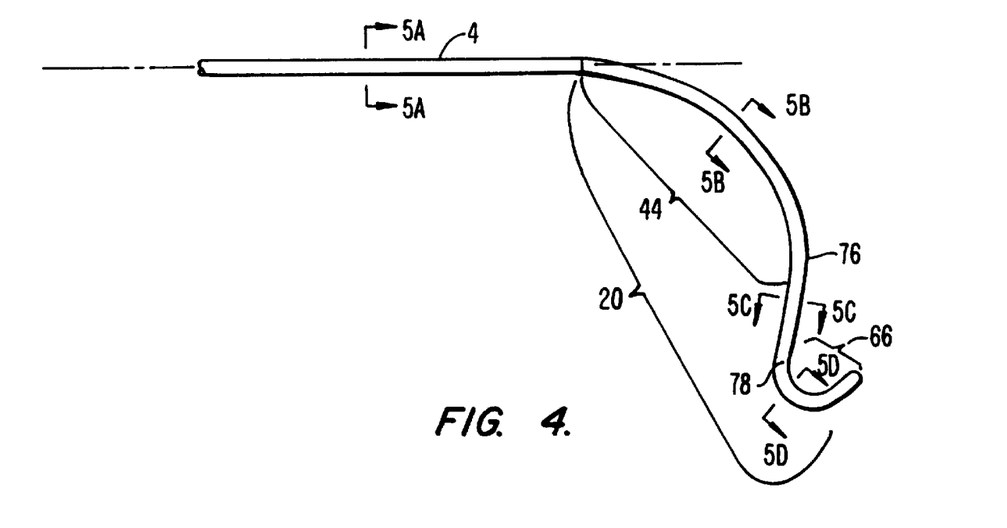
FIG. 4 is a simplified view similar to FIG. 1B and used, in conjunction with FIGS. 5A–5D, to describe how the passage of the manipulator wires through the central and satellite lumens create the various curves.
Figure 5A:
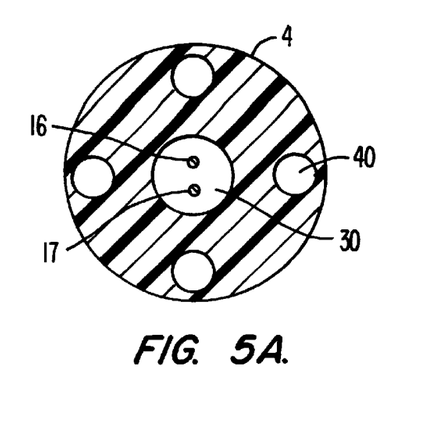
FIGS. 5A–5D are simplified cross-sectional views taken along lines 5A—5A through 5D—5D of FIG. 4.
Figure 5B:
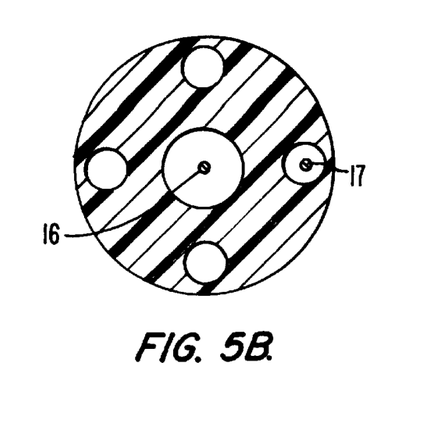
Figure 5C:
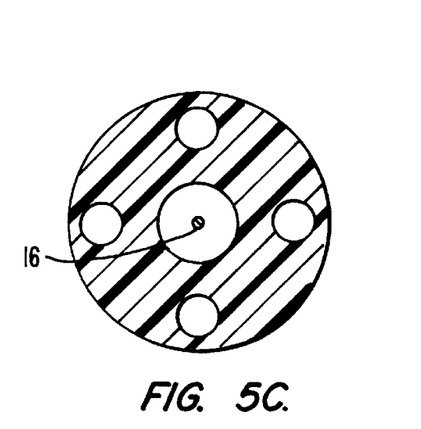
Figure 5D:
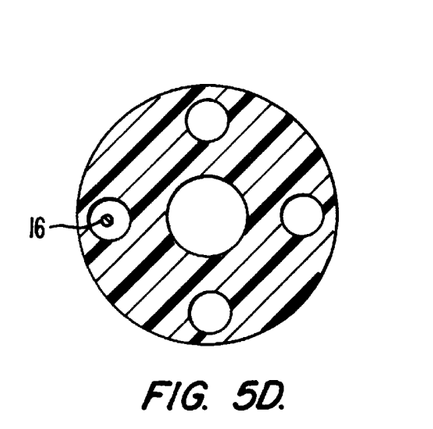

FIGS. 4 and 5A–5D illustrate, in simplified form, the way in which catheter 20 is placed into the dual, recurved form shown in FIGS. 1 and 1B. In this simplified form, catheter shaft 4 is shown to have a main or central lumen 30 and four satellite lumens 40. As shown in FIG. 5A, the two manipulator wires 16, 17, which cause catheter 2 to bend, pass through central lumen 30 until the start of tip 20. At about that point, manipulator wire 17 crosses into one of the satellite lumens 40, as shown in FIG. 5B. Manipulator wire 17 terminates and is secured to the catheter at position 76. This is also shown in FIG. 3B. Therefore, by pulling on manipulator wire 17, that portion of a catheter between position 76 and the start of tip 20, that is proximal segment 44, is bent. The length of the catheter between position 76 and a position 78, which corresponds generally with distal end 56 of insulator 52, as shown in FIG. 2A, finds manipulator wire 16 within central lumen 30 as the manipulator wire passes through electrode 46. At position 78, manipulator wire 16 passes into the satellite lumen 40 opposite the lumen through which manipulator wire 17 had passed. See FIG. 5D. Manipulator wire 16 terminates adjacent tip electrode 70. Pulling on manipulator wire 17 causes distal segment 66 of tip 20 to form the reversed curve bend in the distal segment as shown in FIGS. 1, 1B and 4. As can be seen from FIGS. 4–5D, a great variety of curved segments can be created by passing manipulator wires from a central lumen into side or satellite lumens and then terminating the manipulator wire. For example, if manipulator wire 16 were passed into one of the satellite lumens 40 oriented 90 degrees from the satellite lumen through which manipulator wire 16 passed, distal segment 66 would be curved in a plane about 90 degrees to the plane of the figures. Also, distal curve 66 could deflect in the same plane and same direction as proximal curve 44. In an alternative embodiment, distal curve 66 and proximal curve 44 could be actuated by a single manipulator wire and a single handle control.

Figure 2:
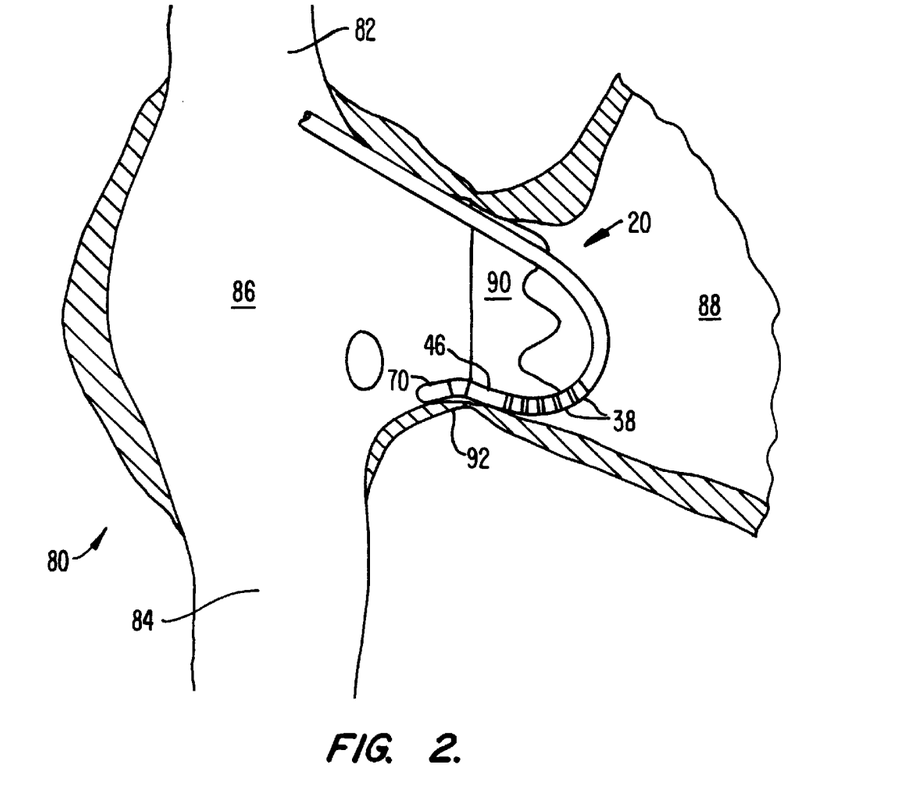
FIG. 2 is a simplified view showing placement of the tip of the catheter of FIG. 1 with the curved proximal segment extending from the right atrium through the tricuspid valve and into the right ventricle, and with the recurved distal segment extending from the right ventricle to engage the annulus of the tricuspid valve.

The use of catheter 2 will now be described with reference to FIGS. 1 and 2. FIG. 2 illustrates, in simplified form, a portion of a heart 80 having a superior vena cava 82 and an inferior vena cava 84 opening into a right atrium 86. Also illustrated is a portion of right ventricle 88 separated from right atrium 86 by a tricuspid valve 90. Tricuspid valve 90 is one of two atrioventricular valves of heart 80. Tricuspid valve 90 has an annulus 92 at the region joining the right atrium 86 with the right ventricle 88.

At times it is desired to ablate tissue on either side of annulus 92. Catheter 2 is especially suited for this purpose. After introducing tip 20 into right atrium 86, tip 20 is maneuvered and manipulator rings 12, 13 are moved to place proximal and distal segments 44, 66 of tip 20 into the shape shown in FIGS. 1 and 2 with distal segment 66 aligned with annulus 92 so that ablation-capable electrodes 46, 70 lie generally on either side of annulus 92. Mapping electrodes 38 are used to take appropriate readings of the electrical activity on the heart surface tissue to help ensure the proper placement of distal segment 66 of tip 20. Once the appropriate readings are taken and distal segment 66 is in the proper position, electrodes 46, 70 can be connected to a suitable RF power supply, such as RF generator 93, through connector 21. One such power supply is shown in U.S. patent application Ser. No. 08/179,558, filed Jan. 10, 1994, the disclosure of which is incorporated by reference. Ablation electrodes 46, 70 are preferably electrically isolated from one another so that they can be independently powered from the power supply. Therefore, the power supply need not be as large as would be required if they were electrically connected to one another or the separate ablation electrodes were replaced by a single, extra long ablation electrode. This eliminates the need to move the ablation electrode after each application of power, the "burn-drag-burn" technique used with conventional ablation catheters.

Typically, a switchbox 94 is connected between the ablation catheter 2 and RF generator 93. Switchbox 94, which can also be connected to an indifferent electrode 96, allows RF current to be directed to any available ablation electrode. Thermocouple signals from the particular electrode, used for temperature monitoring or control, are also supplied to switchbox 94. More than one ablation electrode and thermocouple can be connected simultaneously using switchbox 94. Switchbox 94 can also be automatically controlled.

In the above embodiment, distal segment 66 is placed in its desired reverse curve or recurved shape using manipulator wire 17. This can also be done by pre-forming distal segment 66 to the desired recurved shape.

Figure 6:
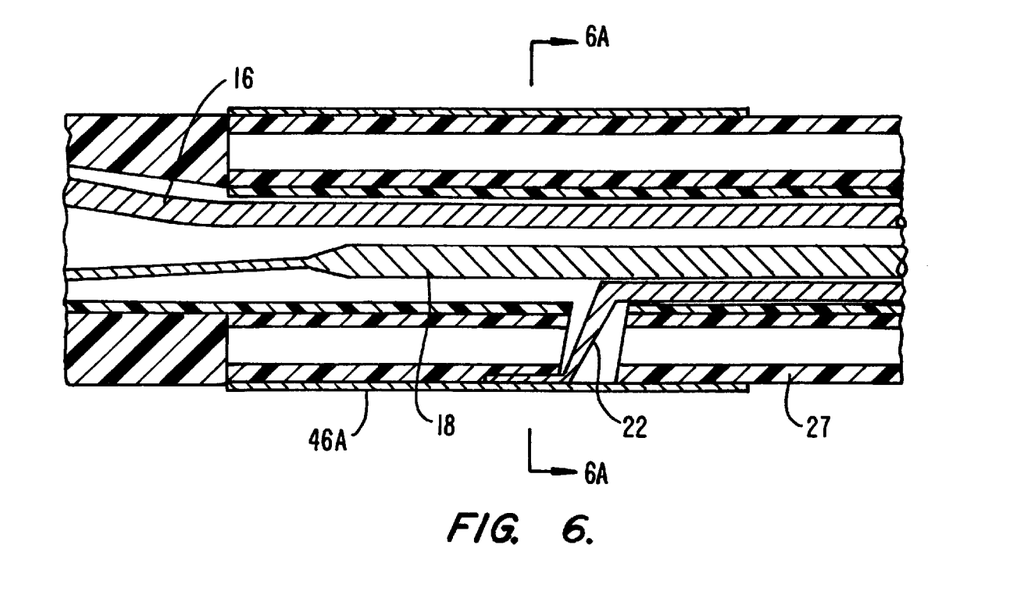
FIGS. 6A and 6B illustrate sections of an alternative embodiment of the catheter shown in FIGS. 3B and 3F.
Figure 6A:
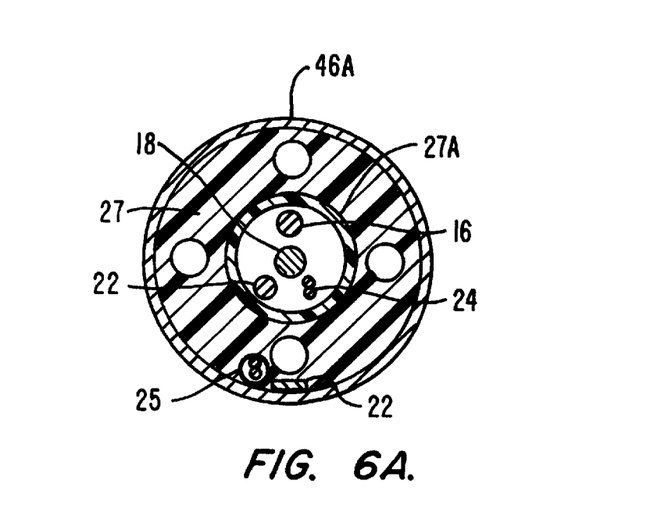

FIGS. 6 and 6A illustrate a section of a catheter similar to that shown in FIGS. 3B and 3F in which cylindrical ablation electrode 46 has been replaced by a sleeve ablation electrode 46A placed about tubing 27 instead of being secured to the distal end of tubing 27 as in the embodiment of FIG. 3D. This eliminates the need to use separate insulators 34, 52 as in the embodiment of FIG. 3D which can result in a simpler and less expensive catheter. In the embodiment of FIGS. 3A–3G, insulators 34, 52, 64 may not be necessary so long as the temperatures of ablation electrodes 46, 70 remain below approximately 100 degrees C. during ablation.

Figure 7:
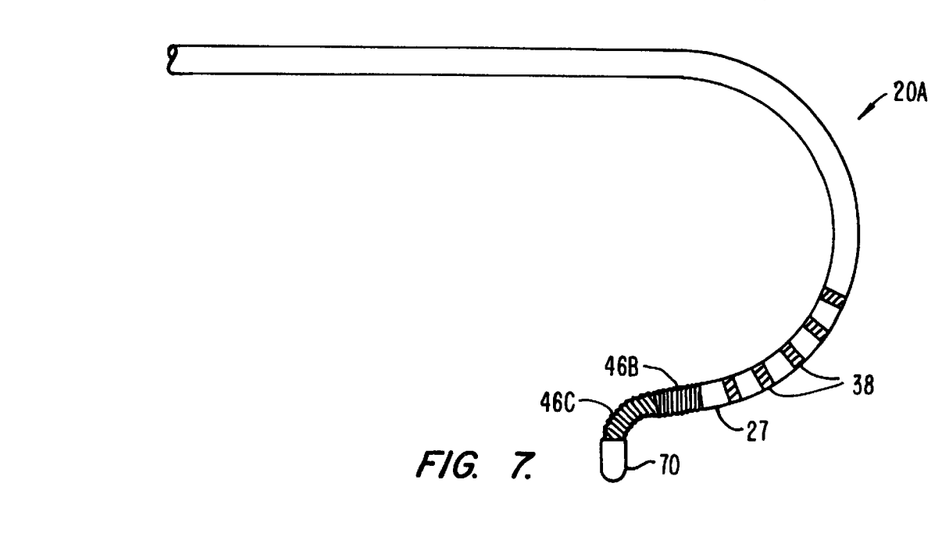
FIG. 7 illustrates the tip of an alternative embodiment of the invention using a coil ablation electrode.
Figure 7A:
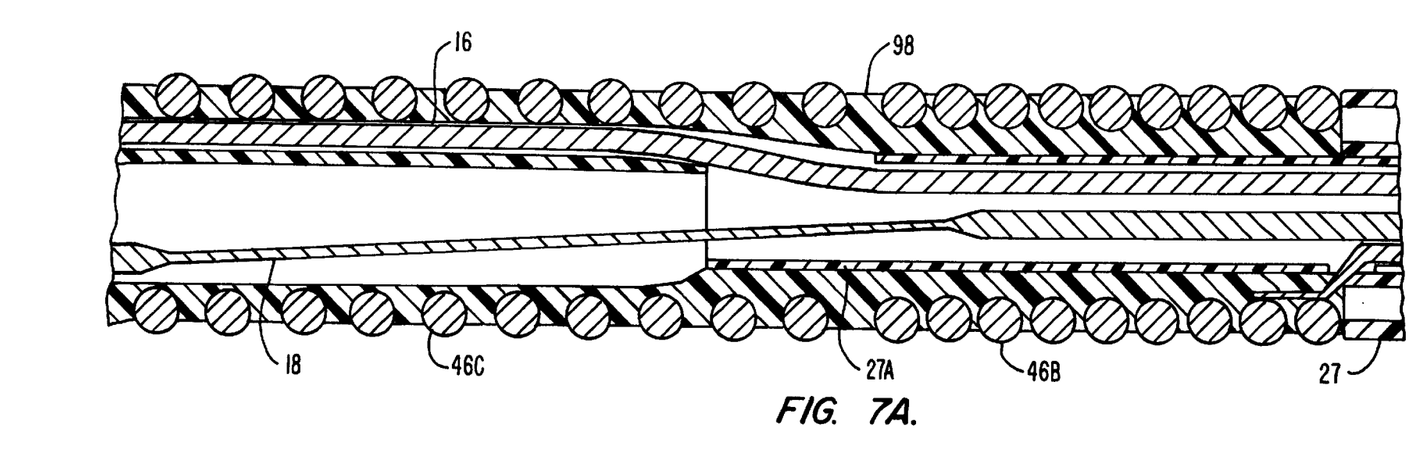
FIG. 7A illustrates a section of the catheter tip of FIG. 7 including the coil ablation electrode.

FIGS. 7A and 7B illustrate another alternative embodiment of catheter 2 in which the solid cylindrical ablation electrode 46 is replaced by a coil ablation electrode, having a first or proximal section 46B with closely spaced coils and a second, more flexible section 46C with more loosely spaced coils, partially embedded within a silicone tube 98. As shown in FIG. 7, electrode section 46C is flexible which can permit the use of an ablation electrode in the curved portion of distal segment 66. Coil electrodes, as well as sleeve and cylindrical electrodes, can have their temperatures monitored using appropriate means, such as thermocouples.

Modification and variation can be made to the disclosed embodiments without departing from the subject of the invention as defined in the following claims. For example, materials, diameters and lengths can be changed to suit the particular needs or desires of the user. A single ablation electrode, or more than two ablation electrodes could be present. Mapping electrodes could also be located between the ablation electrodes. The attachment and bonding techniques discussed above are merely exemplary; other chemical, mechanical and/or thermal bonding techniques can be used as well. In some cases it may be desired to apply energy to more than one ablation electrode at the same time; for example, four ablation electrodes could be used and powered two-at-a-time.

What is claimed is:

1. An ablation catheter comprising:

a shaft having proximal and distal ends with a deflectable tip at the distal end;

said tip including a curvable distal segment and a curvable proximal segment;

at least one ablation-capable electrode positioned along the deflectable tip;

a handle at the proximal end of the shaft;

an ablation energy conductor extending along the shaft between said ablation-capable electrode and the handle; and an actuation mechanism extending distally within the shaft to the deflectable tip, the actuation mechanism adapted to curve the proximal segment in a first direction and to curve the distal segment in a second direction independently of the proximal segment, the proximal and distal segments extending along first and second lengths.

2. The catheter according to claim 1 wherein the at least one ablation-capable electrode is positioned along the distal segment of the deflectable tip.

3. The catheter according to claim 1 wherein the first and second directions are generally opposite from one another.

4. The catheter according to claim 1 wherein the first length is about 3 to 10 times the second length.

5. The catheter according to claim 1 wherein the first length is about 5 times the second length.

6. The catheter according to claim 1 wherein the distal segment is sized and configured to be engagable with an annulus of an atrioventricular valve of a heart to help prevent the distal segment from inadvertently moving from an atrial side to a ventricular side of said atrioventricular valve and to permit proper ablation of tissue adjacent said annulus.

7. The catheter according to claim 6 wherein the atrioventricular valve is a mitral valve.

8. The catheter according to claim 6 wherein the atrioventricular valve is a tricuspid valve.

9. The catheter according to claim 7 wherein the proximal segment is sized to be positionable through the tricuspid valve and into a right ventricle so to stabilize the catheter while ablation energy is delivered to said tissue through said ablation-capable electrode.

10. The catheter according to claim 1 further comprising at least one mapping electrode.

11. The catheter according to claim 1 further comprising a plurality of mapping electrodes.

12. The catheter according to claim 1 wherein the shaft is more flexible at said distal end than at said proximal end.

13. The catheter according to claim 1 further comprising means for applying a torquing force to said distal end of the shaft.

14. The catheter according to claim 13 wherein the torquing force applying means includes a core wire secured to said distal end and extending within a lumen in the shaft between said distal and proximal ends.

15. The catheter according to claim 1 comprising a plurality of said ablation-capable electrodes.

16. The catheter according to claim 15 wherein said electrodes comprise a tip ablation-capable electrode and a circumferential ablation-capable electrode circumscribing the shaft, said electrodes sized and positioned to be engageable with said tissue on both sides of said annulus of said atrioventricular valve.

17. The catheter according to claim 16 wherein each said ablation-capable electrode is connected to a separate one of said ablation energy conductors so that each said electrode can be electrically isolated from all others of said electrodes.

18. The catheter according to claim 1 further comprising a temperature sensor associated with each said ablation-capable electrode.

19. The catheter according to claim 1 wherein the actuation mechanism further comprises:
a movable tip deflector device mounted to the handle; and
an axially movable manipulator wire coupling the proximal segment to the tip deflector device so that selected movement of the tip deflector device causes the manipulator wire to exert a force on said proximal segment causing the curve in said proximal segment.

20. The catheter according to claim 19 wherein the actuation mechanism further comprises:
a second movable tip deflector device mounted to the handle; and
a second axially movable manipulator wire coupling the distal segment to the second tip deflector device so that selected movement of the second tip deflector device causes the second manipulator wire to exert a force on said distal segment causing the curve in said distal segment.

21. An ablation catheter comprising:
a shaft having proximal and distal ends with a deflectable tip at the distal end;
said tip including a curved distal segment and a curved proximal segment;
at least one ablation-capable electrode positioned along the deflectable tip;
a handle at the proximal end of the shaft;
an ablation energy conductor extending along the shaft between said ablation-capable electrode and the handle; and
the proximal and distal segments curving in a first and second directions, the proximal and distal segments extending along first and second lengths;
a movable tip deflector device mounted to the handle; and
an axially movable manipulator wire coupling the proximal segment to the tip deflector device so that selected movement of the tip deflector device causes the manipulator wire to exert a force on said proximal segment causing the curve in said proximal segment;
wherein the shaft includes a central lumen and at least one satellite lumen positioned radially outwardly of the central lumen, the manipulator wire passing through the satellite lumen along said proximal segment and through the central lumen otherwise.

22. The catheter according to claim 21 wherein the shaft includes a second satellite lumen positioned opposite of said satellite lumen, said second manipulator wire passing through the second satellite lumen along the distal segment and through the central lumen otherwise.

23. The catheter according to claim 1 wherein said handle includes an electrical connector connected to the ablation energy conductor.

24. A method for ablation of heart tissue at a target site at an annulus of an atrioventricular valve comprising the following steps:
passing distal and proximal segments of a tip of an ablation catheter into a chamber of a heart of a patient;
manipulating the distal segment of the ablation catheter to a target site at an annulus of an atrioventricular valve;
curving said distal segment in a first curvature to generally conform to the target site, thereby helping to prevent the distal segment from moving from the atrial side to the ventricular side of the atrioventricular valve;
curving the proximal segment in a second curvature while the proximal segment is within a heart of a patient;
placing the curved distal segment against the target site; and
applying ablation energy to an ablation electrode at the distal segment to ablate heart tissue at the target site.

25. The method according to claim 24 wherein the manipulating step is carried out with the target site at a tricuspid valve.

26. The method according to claim 24 wherein the manipulating step is carried out with the target site at a mitral valve.

27. The method according to claim 24 further comprising the step of positioning the proximal segment through an atrioventricular valve.

28. The method according to claim 24 wherein the distal segment curving step is carried out by preshaping the distal segment.

29. The method according to claim 24 wherein the curving steps are carried out so the proximal and distal segments curve in generally opposite directions.

30. The method according to claim 24 further comprising the step of sizing the proximal and distal segments so that the proximal segment has a length about 3 to 10 times the distal segment length.

31. The method according to claim 30 wherein the sizing step is carried out so the proximal segment has a length about 5 times the distal segment length.

32. The method according to claim 24 wherein the ablation energy applying step is carried out by applying ablation energy to a plurality of electrically isolated ablation electrodes spaced apart along at least the distal segment to ablate heart tissue at the target site on either side of the annulus of the atrioventricular valve.

33. The method according to claim 24 wherein the ablation energy applying step is carried out by sequentially applying ablation energy to a plurality of said ablation electrodes.

34. The method according to claim 24 wherein the ablation energy applying step is carried out by simultaneously applying ablation energy to a plurality of said ablation electrodes.

35. The method according to claim 24 wherein the manipulating step includes the steps of selectively applying a torquing force to said distal segment thereby causing said tip, when curved, to move laterally.

36. The method according to claim 24 wherein the curving step is carried out by pulling on a manipulator wire connected to said distal segment passing through a lumen in the catheter shaft.

37. The method according to claim 24 further comprising the step of monitoring the temperature of said electrode.

38. The method according to claim 24 further comprising the step of electrically mapping an area of a heart adjacent the target site.

39. The method according to claim 38 wherein the mapping step is carried out using a mapping electrode mounted to the catheter shaft.

40. The method according to claim 39 wherein the mapping step is carried out using a plurality of mapping electrodes, at least one of said mapping electrodes being located proximal of said ablation electrode.

41. A method for ablation of heart tissue at a target site on either side of an annulus of a tricuspid valve comprising the following steps:

passing distal and proximal segments of an ablation catheter into a right atrium of a heart;

manipulating the distal segment of the ablation catheter to a target site at an annulus of a right atrioventricular valve;

curving said distal segment in a first curvature to generally conform to the target site, helping to prevent the distal segment from moving from the atrial side to the ventricular side of the atrioventricular valve;

curving the proximal segment in a second curvature, the first and second curvatures curving in generally opposite directions;

positioning the proximal segment through the right atrioventricular valve;

placing the curved distal segment against the target site; and applying ablation energy to at least one ablation electrode at the distal segment to ablate heart tissue at the target site.

42. The method according to claim 41 wherein the passing step includes the step of passing the distal segment into the superior vena cava.

43. The method according to claim 41 further comprising the step of sizing the proximal and distal segments so that the length of the proximal segment is at least 5 to 15 times the length of the distal segment.

44. The method according to claim 41 further comprising the step of mapping a portion of a right ventricle in the vicinity of the target site.

45. A method for ablation of heart tissue at a target site on either side of an annulus of a mitral valve comprising the following steps:

passing distal and proximal segments of an ablation catheter transaortically through an aortic valve and into a left ventricle;

manipulating the distal segment to a target site at an annulus of the mitral valve;

curving said distal segment in a first curvature to generally conform to the target site to help prevent the distal segment from moving from the target site;

curving, within the heart, the proximal segment in a second curvature, the first and second curvature curving in generally opposite directions;

placing the curved distal segment against the target site; and applying ablation energy to at least one ablation electrode at the distal segment to ablate heart tissue at the target site.

46. The method according to claim 45 further comprising the step of sizing the proximal and distal segment so that the length of the proximal segment is at least about 5 to 15 times the length of the distal segment.

47. An ablation catheter as claimed in claim 1, wherein the first and second directions are generally opposite from one another.

48. An ablation catheter comprising:

a shaft having a proximal end, a distal end, a shaft centerline, and a deflectable tip at the distal end;

said tip including a curved distal segment and a curved proximal segment, the proximal segment curving in a first direction;

at least one ablation-capable electrode positioned along the deflectable tip;

a handle at the proximal end of the shaft;

an ablation energy conductor extending along the shaft between said ablation-capable electrode and the handle; and a first axially movable manipulator wire within the shaft along the proximal and distal segments, the first manipulator wire disposed near a shaft centerline along the proximal segment, the first manipulator wire radially offset from the shaft centerline along the distal segment to curve the distal segment in a second direction which is different than the first direction.

49. An ablation catheter as claimed in claim 48, further comprising a second axially movable manipulator wire within the shaft along the proximal segment, the second wire radially offset from the shaft centerline along the proximal segment and angularly offset about the shaft centerline from the first manipulator wire along the distal segment, the manipulator wires being disposed near a shaft centerline proximally of the deflectable tip.

50. A method for ablation of heart tissue at a target site at an annulus of an atrioventricular valve comprising the following steps:

passing distal and proximal segments of a tip of an ablation catheter into a chamber of a heart of a patient;

manipulating the distal segment of the ablation catheter to a target site at an annulus of an atrioventricular valve, the distal segment being a precurved segment and curving in a first curvature to generally conform to the target site, thereby helping to prevent the distal segment from moving from the atrial side to the ventricular side of the atrioventicular valve;

curving the proximal segment in a second curvature while the proximal segment is within a heart of a patient;

placing the curved distal segment against the target site; and applying ablation energy to an ablation electrode at the distal segment to ablate heart tissue at the target site.

* * * * *